United States Patent [19]

Brooks

[11] Patent Number: 5,035,717

[45] Date of Patent: Jul. 30, 1991

[54] INSERT AND METHOD OF USING SAME

[76] Inventor: Peter J. Brooks, 3 L'Estrange Place, Toronto, Ontario, Canada, M6S 4S6

[21] Appl. No.: 248,745

[22] Filed: Sep. 26, 1988

[30] Foreign Application Priority Data

May 12, 1988 [CA] Canada ................................. 566572

[51] Int. Cl.$^5$ .......................... A61F 2/32; A61F 2/30
[52] U.S. Cl. ....................................... 623/18; 623/23
[58] Field of Search ....................... 623/16, 18, 19, 20, 623/21, 22, 23

[56] References Cited

U.S. PATENT DOCUMENTS

| | | | |
|---|---|---|---|
| 4,336,618 | 6/1982 | Raab | 3/1.913 |
| 4,406,023 | 9/1983 | Harris | 623/23 |
| 4,430,761 | 2/1984 | Niederer | 3/1.91 |
| 4,491,987 | 1/1985 | Park | 3/1.91 |
| 4,536,894 | 8/1985 | Galante | 623/22 |
| 4,662,891 | 5/1987 | Noiles | 623/22 |
| 4,676,798 | 6/1987 | Noiles | 623/23 |
| 4,678,472 | 7/1987 | Noiles | 623/1.8 |
| 4,698,063 | 10/1987 | Link et al. | 623/23 |
| 4,718,909 | 1/1988 | Brown | 623/16 |
| 4,718,912 | 1/1988 | Crowinshield | 623/23 |
| 4,718,914 | 1/1988 | Frey | 623/23 |
| 4,718,915 | 1/1988 | Epinette | 623/23 |
| 4,718,916 | 1/1988 | Morscher | 623/23 |
| 4,753,657 | 6/1988 | Lee et al. | 623/23 |
| 4,790,852 | 12/1988 | Noiles | 623/23 |

FOREIGN PATENT DOCUMENTS

| | | | |
|---|---|---|---|
| 172883 | 5/1986 | European Pat. Off. | |
| 2645100 | 4/1978 | Fed. Rep. of Germany | 623/23 |
| 2726297 | 12/1978 | Fed. Rep. of Germany | 623/18 |
| 3334058 | 4/1985 | Fed. Rep. of Germany | 623/22 |
| 181918 | 6/1978 | New Zealand | 623/23 |
| 2104391 | 3/1983 | United Kingdom | 623/22 |

OTHER PUBLICATIONS

Design Features and Early Clinical Results with a Modular Proximally Fixed Low Bending Stiffness Uncemented Total Hip Replacement, 1988, Cameron.
Joint Medical Products Brochure, ©1984, for S-Rom 135.
Joint Medical Products SNR Total Hip and Stem Collar System.
Indications for the Use of a Constrained THR Prothesis, Jan. 1981.
Dislocations after Total Hip Arthoplasty, Dec., 1982.
Joint Medical Products Corp., Product News release #1, May 15, 1984.
S-Rom 135th Femoral Stem, 2-28-84.
Harris Galante Porous Hip Prothesis, ©1987, Zimmerman, Inc.
S-Rom Modular Total Hip System, ©1988.
S-Rom Poly-dial Acetabular System, ©1988.
S-Rom System Indexability.
Rothman Institute Hip Program, Bionet Inc.

Primary Examiner—David J. Isabella
Attorney, Agent, or Firm—Rogers, Bereskin & Parr

[57] ABSTRACT

This invention relates to a femoral insert for a hip joint prothesis for use in a femur that has been cut across the femoral neck to form a cut surface. The insert includes a stem having a proximal end attachable to a generally spherical head member, a distal end and a bend located therebetween. A collar is provided for transferring axial loads from the stem to the femur at the cut surface. A sleeve is secured within the femur, the sleeve having a central orifice for receiving the stem. The sleeve permits the stem to move axially but restricts the stem from any rotational or toggling movement. The sleeve is secured into the femur below the cut surface.

19 Claims, 3 Drawing Sheets

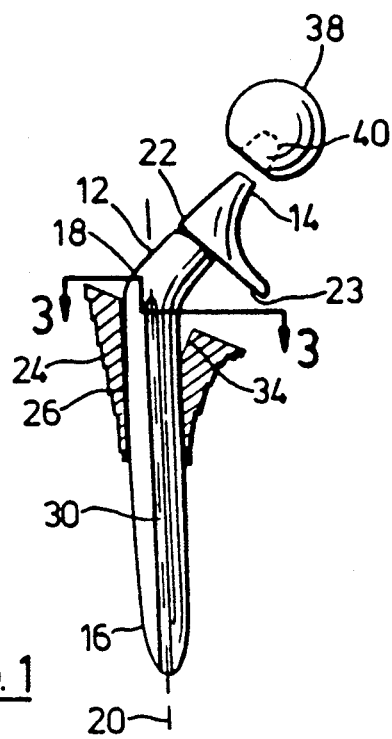
FIG.1
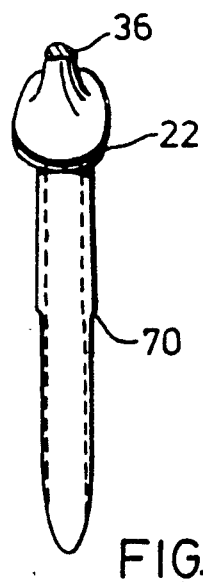
FIG.2
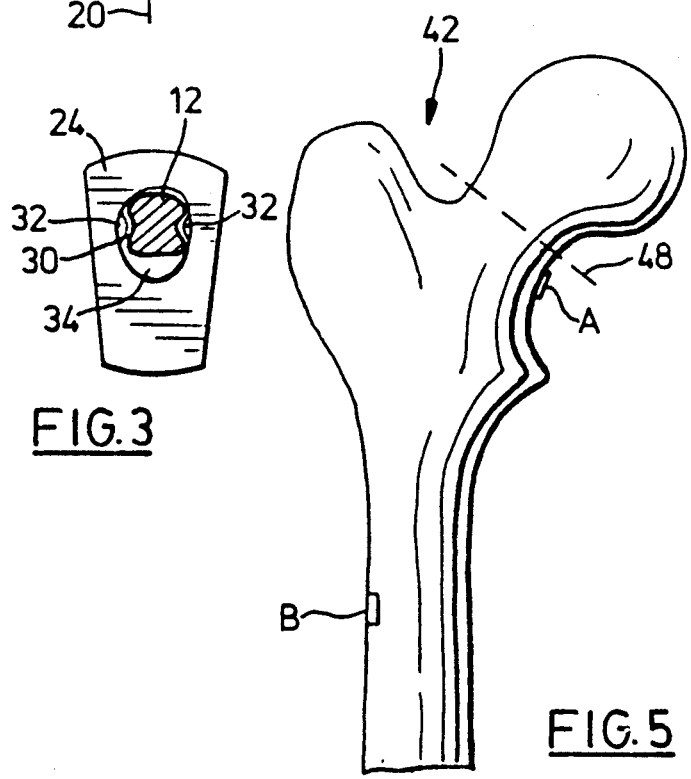
FIG.3
FIG.5

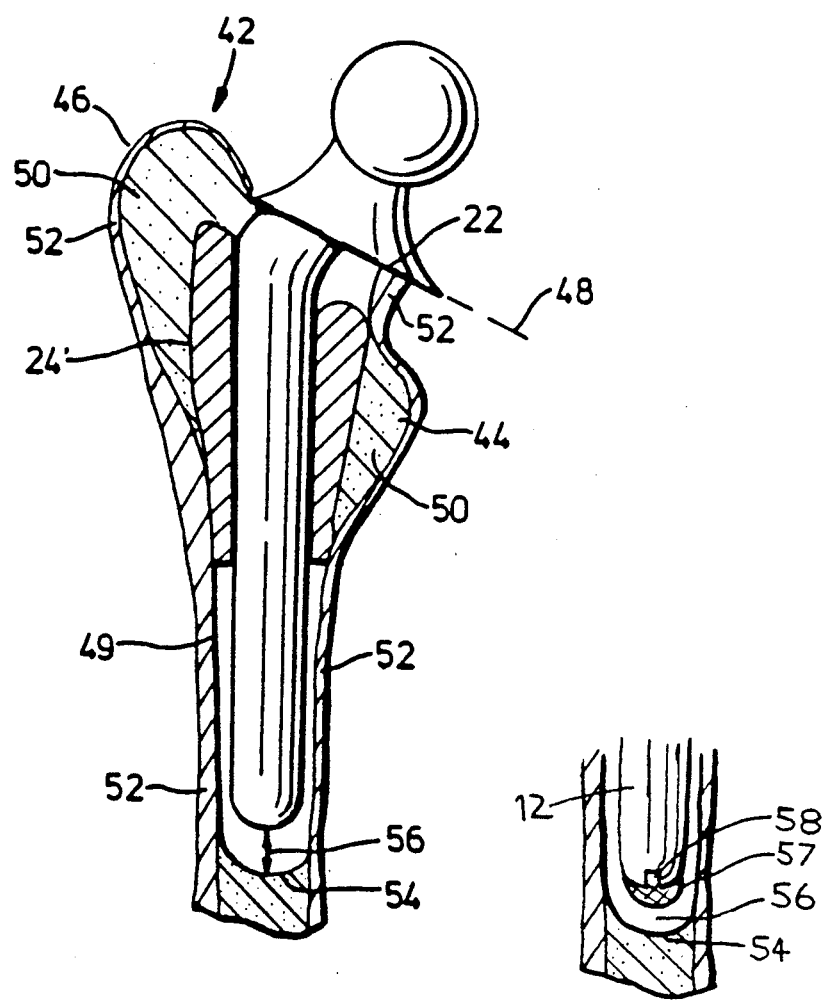

INSERT AND METHOD OF USING SAME

FIELD OF THE INVENTION

This invention relates to an insert of the type used in a hip joint prothesis. In particular, this invention relates to the type of insert that may be inserted into the upper end of the femur to replace an otherwise damaged femoral head.

BACKGROUND OF THE INVENTION

Total hip replacement, through the use of a hip prothesis, is one of the most successful recent medical innovations. However, it has become apparent that in the long term, an implanted hip prothesis commonly encounters problems. The most common form of implant failure, once the medical operation of insertion of the implant has successfully been completed, is eventual loosening of the implant within the femur. While revision surgery is possible, success rates are much lower than in primary cases and the incidence of complications (such as infection, dislocation and loosening) following the new surgical operation is higher. Failure often occurs earlier in revision cases.

The loosening of the hip prothesis is a multi-factorial process. Mechanical factors, related to stress distribution within the femur bone itself, and biological factors relating to resorption of the bone of the femur, both have a role.

Typically, prior to implanting a femoral prothesis, the head of the femur has been removed by cutting across the neck. The femoral prothesis is then inserted into the femur which has a profound effect upon the stress distribution within the proximal femur. In a normal proximal femur weight bearing is transferred directly to the thick cortex of the medial femoral neck, or calcar femorale. In contrast, after implantation of a conventional hip prothesis, most of the weight bearing by-passes this portion of the femoral neck and is transferred distally to the tip of the implant stem.

In experimental study in relation to conventional hip inserts, it has been found that a massive decrease in stress in the region of the thick cortex of the medial femoral neck occurs after implantation (Oh and Harris; Proximal Strain Distribution In The Loaded Femur: Journal of Bone And Joint Surgery. 60A - : 75 January, 1978). The study concluded that this so called stress shielding is likely responsible for resorption of the thick cortex of the medial femoral neck which is seen in up to 70% of hip replacements.

There have been attempts in the prior art to restore loading to the cortex of the medial femoral neck by adding a collar to the femoral prothesis. However, the prior art devices rely on some form of attachment between the femoral insert and the inner surface of the femur such as by using wedge shaped stems or cementing or bonding the stem of the femoral insert to the femur itself. This makes it difficult, if not impossible, to ensure that a good contact is made between the collar and the thick cortex of the medial femoral neck. In addition, it fails to transmit forces adequately to the calcar femorale. Further, a small amount of resorption, induced by for example, surgical trauma, stress shielding or vascular interruption could unseat the collar thereby making the collar useless.

Therefore, what is desirable, is to provide a femoral prothesis which will reliably transfer the bulk of weight bearing directly to the thick cortex of the medial femoral neck.

BRIEF SUMMARY OF THE INVENTION

Therefore, it is an object of the present invention to provide an insert which includes improved means for transferring weight from the insert to the femur. Accordingly, in one of its aspects, the invention provides a femoral insert for a hip joint prothesis for use in a femur that has been cut across the femoral neck to form a cut surface, the insert comprising a stem having a proximal end attachable to a generally spherical head member, a distal end and a bend located therebetween, the stem having a longitudinal axis below the bend, a load transferring means for transferring axial loads from said stem to said femur at said cut surface, and a guide means for locating said stem within said femur, said guide means and said stem cooperating to permit axial movement along said longitudinal axis, but to restrict any other movement of said stem within said guide means, said guide means being securable to said femur below said cut surface.

BRIEF DESCRIPTION OF THE DRAWINGS

FIG. 1 is a view partly in cross section of one embodiment of the present invention;

FIG. 2 is a side view of an element of the invention of FIG. 1;

FIG. 3 is a cross sectional view through lines 3—3 of FIG. 1;

FIG. 4 is a view showing a second embodiment of the invention in position in a femur;

FIG. 4a is a view showing an alternate embodiment of the invention of FIG. 4;

FIG. 5 is a view of a femur indicating strain gauge locations A and B;

FIG. 1 shows an insert according to the present invention and indicated generally at 10. The insert is formed of a stem 12 having a proximal end 14, a distal end 16 and a bend 18 therebetween. The stem 12 is generally of uniform cross section and has a longitudinal axis below the bend 18 indicated as 20.

Figure 6:
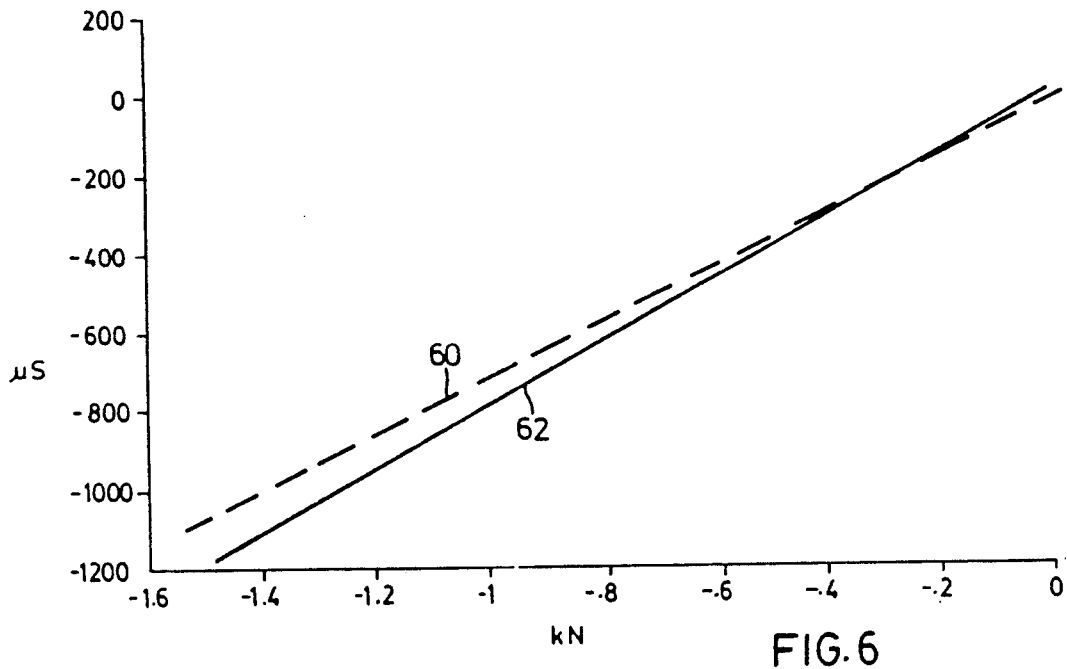
FIG. 6 is a graph showing the relationship between the loading and strain in a normal femur and in a femur having an insert according to the present invention at a location A as shown in FIG. 5.

Between the bend 18 and the proximal end 14 is located a collar 22. The collar 22 is securable to the stem 12 and in some cases the collar 22 may preferably be integrally formed with the stem 12. In essence, the collar 22 is a means for transferring axial loads from the stem to a femur as described below.

Also shown in FIG. 1 is a sleeve 24 which has a central bore 26 which is of slightly larger diameter than the diameter of the stem 12 below the bend 18. The stem 12 below the bend 18 cooperates with the sleeve 24 to allow axial movement of the stem 12. However, any movement other than axial movement is to be avoided. Therefore, the clearance between the central bore 26 and that portion of the stem 12 that fits therein should be sufficiently small to prevent unwanted movement of the shaft laterally within the sleeve (which may be referred to as "toggling"), while at the same time allowing for a sliding axial movement. The sleeve 24 is in essence a guide means for locating the stem 12 within a femur, when the insert 10 is in position.

As best seen in FIG. 3 a pair of opposed grooves 30 are provided in the stem 12 below the bend 18. A pair of ridge 32 which mate with the opposed grooves 30 are provided in the sleeve 24. In this manner, the stem 12 while permitted to move axially along the longitudinal axis 20 within sleeve 24 is restricted from any rotational movement about longitudinal axis 20 or toggling. In essence, the sleeve 24 is a means for guiding and locating the stem 12 within a femur, which permits axial movement of the stem 12 along the longitudinal axis 20 but restricts rotational movement of the stem 12 about the longitudinal axis 20. The sleeve 24 is securable in a femur in a manner described below. It will be appreciated by those skilled in the art that the use of mating grooves 30 and ridges 32 is only one manner of achieving the desired results. Provided that rotational movement or toggling is restricted, while allowing axial movement, any configuration of central bore and stem cross-section is permissible. Essentially, any mating non-circular cross-section will perform the same function.

The inner surface of the sleeve may be lined with a layer of ultra-high molecular weight polyethylene to minimize friction and wear at the stem-sleeve interface.

Also shown in FIGS. 1 and 3 is a sloped shoulder 34 at one side of the top end of bore 26. It will be appreciated from FIG. 1 that the sloped shoulder 34 permits the stem 12 somewhat further axial movement than would otherwise be the case, by accommodating a portion of the bend 18 therein.

As can be seen from FIGS. 1 and 2, the proximal end 14 of the stem 12 includes a tapered conical section 36. Also shown in FIG. 1 is a generally spherical head member 38 which as shown in ghost outline has a tapered orifice 40. Upon insertion of the tapered section 36 of the proximal end 14 into the tapered orifice 40 the spherical head member 38 becomes firmly secured to the proximal end 14 of the stem 12. The secure attachment is achieved by means of the taper of the section 36 being similar to the taper of the orifice 40, so that a frictional fit therebetween is achieved. This is commonly known as a Morse taper. Other methods of attachment of the head 38 to the stem 12 such as welding or the like could also be used. Alternatively, the generally spherical head member 38 may be integrally formed with the stem 12.

Turning to FIG. 2, it can be seen that the collar 22 is of generally rounded oblong appearance when viewed from above. The collar 22 may be of any shape, provided that it extends sufficiently to seat against the thick cortex of the medial femoral neck as described below. Turning now to FIG. 4, it may now be appreciated how the femoral insert of the present invention may be put into effect. In FIG. 4 is shown a femur in cross section and indicated generally at 42. Shown at 44 is the lesser trochanter and at 46 is the greater trochanter. The femoral head has been cut off, and a cut surface has been formed along line 48. As shown in FIG. 4, the femur is comprised of two different types of bone. The first type indicated at 50 is known as trabecular bone. A second type shown at 52 is known as cortical bone. Typically, the cortical bone 52 is stiffer and stronger than the trabecular bone 50. The cortical bone 52 forms a tough outer shell or skin over the trabecular bone 50 which together form the femur 42.

As shown in FIG. 4, a second embodiment of the sleeve, indicated as 24' has been inserted into the intertrochanteric area of the proximal femur. The sleeve 24' is identical in function to the sleeve 24 shown in FIGS. 1 and 3. The collar 22 is shown resting against the cut surface 48 of the femoral neck. The collar 22 extends medially far enough to provide a firm seat against the femur 42 and in particular against the outer rim of cortical bone 52 that is present around the cut surface 48 of the femur 42.

The sleeve 24' may be secured within the femur in any number of ways. Firstly, the sleeve may be cemented in place, through the use of bone cement. Alternatively, the sleeve may be provided with a beaded or otherwise stippled outer surface which is amenable to bone ingrowth. In a further alternative, the sleeve may be formed of a generally tapering cross section and may be force-fit into the proximal femur. It will be appreciated by those skilled in the art that any of these alternatives, or even combinations thereof, may provide satisfactory results.

Prior to insertion of the femoral insert 10 into the femur, the femur must be prepared. In addition to making the cut surface 48, the center of the femur is reamed, to form a channel 49, so that the distal end 16 of the item 12 can be inserted therein. Typically, the diameter of the channel 49 is about 0.5 mm greater than the diameter of the stem 12 near the distal end 16. Typically there is a small clearance between the bottom of the distal end 16 of the stem 12, and the bottom of the opening 54 which is formed in the femur to accommodate the stem 12. This clearance is slightly exaggerated in FIG. 4 and is indicated at 56. Clearance 56 ensures that the stem 12 does not seat and transfer significant forces to the bottom of opening 54, since that would defeat the object of having the load transferred by collar 22 to the cut surface 48. It will be appreciated by those skilled in the art that the clearance 56 is preferred, but that due to the yielding nature of trabecular bone 50, it may not be essential. As shown in FIG. 4a, a compressible non-metallic tip 57 may be fixed to the end of the stem 12 to minimize axial support of the stem 12 should there occur later growth of bone in clearance 56. The tip 57 would be made, for example, from a lattice of ultra-high molecular weight polyethylene and could be secured, for example, by being threaded into a threaded opening 58 in the distal end of stem 12.

The preferred material for both the sleeve 24 or 24' and the stem 10 is metal. In particular, a solid alloy of cobalt chrome is preferred, having a general composition of about 60–65% cobalt, 30% chromium, 6% molybdenum, 1% nickel and about 0.35% carbon (ASTM F-75-82; F-799-82). This provides a material that is suitable for its intended use as a hip replacement, although those skilled in the art will realize that other metal alloys may also be suitable.

It can now be appreciated that the femoral insert according to the present invention provides a loading of the femur 42 which emulates physiological loading of a natural femur. The stem 12 is free to move axially along longitudinal axis 20 within the sleeve 24 or 24'. Thus, under loading of the spherical head member 38 weight is transferred to the proximal end 14 of the stem 12 and then to the collar 22. From the collar 22 the weight is transferred to the cut surface 48 of the femoral neck, and in particular is transferred to the thick cortex of the medial femoral neck. Resorption of the bone under the cut surface can be accommodated by the present invention by means of axial movement of the stem 12 within sleeve 24 or 24'. Therefore, it can now be appreciated that the present invention allows for a continued secure seating of the collar 22 on the cut surface 48 of the femoral neck. Further, the present invention allows the thick outer cortex of the medial femoral neck to be loaded, which emulates natural physiological loading. Therefore, stress shielding of this portion of the proximal femur, which is a feature of the prior art devices, will be reduced, with the consequent reduction in bone resorption.

EXAMPLE 1

To test the effectiveness of loading of the cortical bone 52 of the femur by the present invention, a hip implant simulator was developed to study the stress transmission of the insert 10. Essentially, strain gauges were attached to a natural femur which was then loaded under axial loading. The resulting strains under different axial loads were measured and plotted. In FIG. 5 is shown the approximate location of two strain gauges A and B. Once the measurements were made with the natural femur the head of the femur was cut off to form a cut surface 48. Then the insert 10 of the present invention was inserted within the femur and the femur was again loaded in a manner identical to the loading of the natural femur. Again, the strain readings for different loads were measured, and plotted beside the measurements for the natural femur.

In FIG. 6 the results of the strains recorded by strain gauge A are plotted. The vertical axis is strain, measured in microstrain while the horizontal axis is force, measured in kilonewtons. The dashed line 60 represents the strain resulting from the loading of the insert 10. The solid line 62 represents the strain for the same loading of the natural femur. As can be seen, the lines are very close and the strain measured in the cortical bone 52 with the insert closely matches that of the natural femur.

Figure 7:
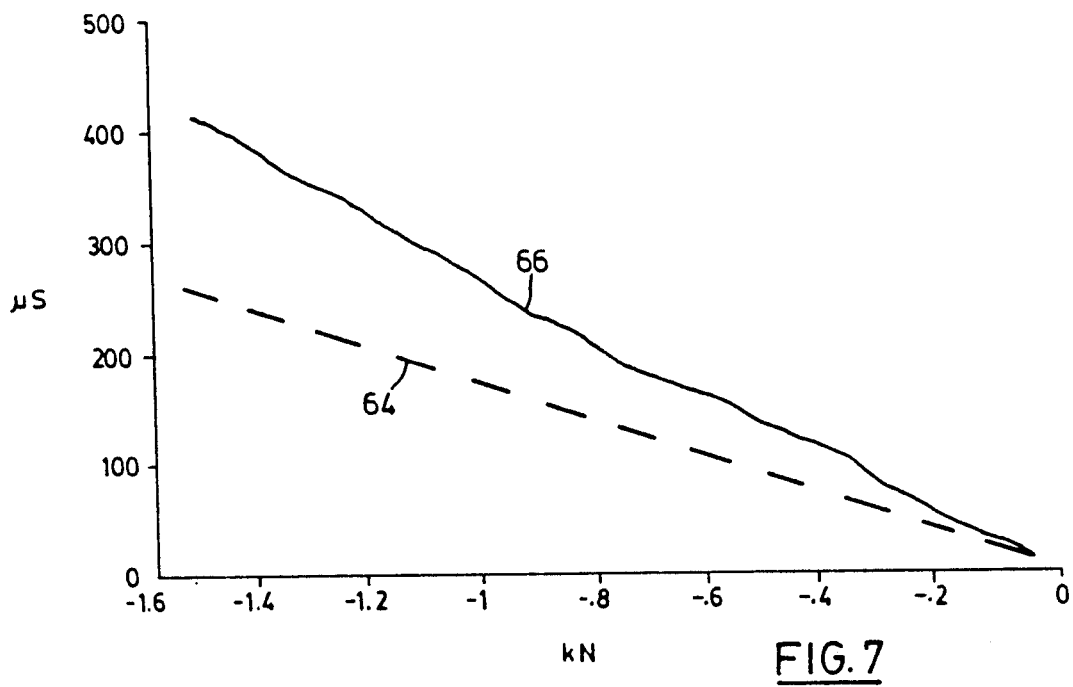
FIG. 7 is a graph showing the relationship between the loading and strain for a normal femur and for a femur having an insert according to the present invention at a location B as shown in FIG. 5.

Referring to FIG. 7, the strain at strain gauge B is plotted in microstrain against force in kilonewtons on the stem 12. Again, the strain measured in the insert 10 is shown as a dotted line 64 and the strain measured with the natural femur is shown as a solid line 66. Again, the insert 10 generally follows the strain of the natural femur although for a given loading somewhat greater strain is present in the natural femur. This indicates that perhaps the insert 10 imposes slightly smaller tensile forces on the femur at strain gauge B than the natural femur experiences. Tables showing the actual plotted values follow:

TABLE 1

| STRAIN GAUGE A | | | |
|---|---|---|---|
| Natural Femur | | Insert | |
| Force (KN) | Strain ($\mu$S) | Force (KN) | Strain ($\mu$S) |
| −.004 | 0 | .0001 | 0 |
| −.401 | −313.8 | −.393 | −303.5 |
| −.786 | −617.5 | −.815 | −607.0 |
| −1.20 | −941.4 | −1.184 | −849.8 |
| −1.51 | −1,184 | −1.53 | −1072.4 |

TABLE 2

| STRAIN GAUGE B | | | |
|---|---|---|---|
| Natural Femur | | Insert | |
| Force (KN) | Strain ($\mu$S) | Force (KN) | Strain ($\mu$S) |
| −.004 | 0 | .0001 | 0 |
| −.401 | 112.9 | −.393 | 61.5 |
| −.786 | 205.2 | −.815 | 133.3 |
| −1.20 | 328.3 | −1.184 | 205.1 |
| −1.51 | 410.4 | −1.53 | 266.6 |

In another aspect of the present invention, the undersurface of the collar 22, which is shown as 23 in FIG. 1, may be provided with a surface which is amenable to bone ingrowth. The undersurface 23 seats directly on the cut surface 48 and in particular on the thick cortex of the medial femoral neck. The cortex 52 anticipated to be a good site for developing bone ingrowth. Further, the continued axial loading of the collar 22 on the cut surface 48 is also anticipated to be condusive to bone ingrowth. As previously indicated, surfaces which are condusive to bone ingrowth include beaded, plasma sprayed, sintered mesh or other suitably textured surfaces.

To accommodate differences in physiology, it is desirable to taper the distal end 16 of the stem 12. In this sense, a taper may be a gradual taper, or may be by means of one or more small step changes which narrow the radius of the stem 12. One such a step change is shown as 70 in FIG. 2. Also, to ensure that the distal end 16 of the stem 12 does not jam against the femoral bone thereby potentially restricting axial movement of the stem 12 and defeating the purpose of the present invention it is preferable to have a smoothly rounded or tapered tip at the distal end 16.

In terms of surgical technique, the proximal femur can be exposed using any standard surgical technique. The next step is to cut across the femural neck along line 48. An oscillating saw is appropriate for this task. In addition, a neck-cutting guide may be used to assist in roughly determining the angle of the cut line 48.

The next step is to ream the femoral canal to a predetermined desired diameter. The diameter will be determined by examining pre-operation X-rays and by using appropriate templates.

Then, the next step is to attach a sleeve broach to a handle and broaching guide, which is of a matching size to that of the reamer used in the previous step. Then it is necessary to broaden the proximal femur to accept the sleeve 24. Next, the broach is left in place, the handle is detached from the broach, and an axle is exposed. The cut surface of the calcar is then made flat and smooth with a calcar rasp mounted on the axle. Then all the surgical tools are removed. Next, the sleeve 24 is inserted into the proximal femur holding it in position with the broaching guide or the like. As indicated the sleeve may be cemented, press fit or in some other manner retained in the femur. Finally, the stem 12 is inserted into the sleeve 24 having regard to obtaining a correct neck length and head size.

It will be appreciated by those skilled in the art that many variations are possible within the broad scope of the present invention. Some of these have been suggested above and others will be apparent to those skilled in the art. For example, while reference has been made to the generally oblong collar 22, it will be appreciated that any shape of the collar 22 will be sufficient provided that the collar 22 seats against the thick cortex of the medial portion of the femoral neck. Also, while various methods of attaching the sleeve 26 have been indicated, other method that secure the sleeve 26 within the intertrochanteric area of the femur may also be suitable, provided rotation movement and toggling of the stem 12 are restricted.

I claim:

1. A femoral insert system for a hip joint prothesis for use in a femur that has been cut across the femoral neck to form a resected surface, the insert system comprising:
    a prothesis having an enlarged portion at a proximal end thereof: a generally spherical head member attachable to said enlarged portion; a stem having an outer surface extending from said enlarged portion to a distal end thereof, said stem having a bend located adjacent said enlarged portion and defining a longitudinal axis below said bend, wherein said enlarged portion extends radially outwardly beyond the outer surface of the stem for transferring axial loads from the spherical head member to the resected surface of the femur, and
    a guide means interior passageway configured for slideably housing said stem within said femur said guide means being securable to the femur below said resected surface, and said interior passageway and said stem, for at least a portion of said stem between said bend and said distal end, having mating axially non-interfering cross-sectional profiles to permit free axial movement of said stem along said longitudinal axis, and restricting rotational or toggling movement of said stem relative to said guide means, said guide means being securable to said femur below said resected surface.

2. The insert system of claim 1 wherein said enlarged portion comprises a collar securable to said stem, said collar being sized for contacting said femur at an outer cortical bone section, and when said insert is in position, said collar transferring axial loads from said stem to said cortical bone section.

3. The insert system of claim 2 wherein said collar has an undersurface for seating against said resected surface of said femoral neck, said undersurface including means conducive to bone ingrowth.

4. The insert system of claim 1 wherein said guide means and said stem have cross-sectional profiles which cooperate to restrict rotational movement of said stem about said longitudinal axis and further restrict movement of said stem in any direction, perpendicular to said longitudinal axis.

5. The insert system of claim 1 wherein said guide means is a sleeve, having a central bore for receiving said stem therein.

6. The insert system of claim 5 wherein said stem is of generally uniform cross-section for that portion of the stem cooperating with the sleeve.

7. The insert system of claim 5 wherein said sleeve has an outer surface including means conducive to bone ingrowth.

8. The insert system of claim 5 wherein said sleeve having a generally tapered in outer contour and may be force fit into said femur.

9. The insert system of claim 5 wherein said central bore has a proximal region which is enlarged for accommodating said bend of said shaft.

10. The insert system of claim 1 wherein said stem has a non-circular cross section below said bend, and said guide means comprises a sleeve having a corresponding, but slightly larger central bore which is non-circular in cross-section, said stem freely moving axially, in said bore, but said bore restraining said stem from rotating about said longitudinal axis or moving in a direction generally perpendicular to said axis.

11. The insert of claim 9 wherein said stem has a pair of opposed grooves running parallel to said longitudinal axis below said bend, and said sleeve has a pair of opposed ridges mating with said grooves.

12. The invention of claim 1 wherein said stem at said distal end, tapers to a rounded tip.

13. The invention of claim 12 wherein there is a slight reduction in the thickness of said stem near to said distal end, so that said distal end of said stem is narrower than a portion of the stem between said distal and said proximal ends.

14. The invention of claim 1 wherein said stem includes a compressible non-metallic tip attached to said distal end.

15. The invention of claim 14 wherein said tip comprises a lattice of ultra high molecular weight polyethylene.

16. A femoral insert system for a hip joint prothesis for use in a femur that has been cut across the femoral neck below its head to form a resected surface, the insert system comprising:
    a prothesis having a generally spherical head member attachable to a proximal end thereof, and a stem extending from said proximal end to a distal end, said stem having a bend located adjacent said enlarged portion and defining a longitudinal axis below said bend,
    a load transferring collar securable to said stem between said proximal end and said bend, said collar extending radially outwardly for transferring axial loads from the spherical head member to the resected surface of the femur when said prosthesis is in position, and
    a tapered sleeve securable within said femur below said resected surface when said prothesis is in position, said sleeve having a bore configured to allow free axial movement of said stem along said longitudinal axis, thereby allowing seating of said collar onto said resected cortical bone section, said bore restraining rotational movement of said stem about said longitudinal axis, thereby maintaining said proximal end, when said insert is in position, in position.

17. A femoral insert system for a hip joint prosthesis for use in a femur that has been out across the femoral neck to form a resected surface, the insert system comprising:
    a prothesis having a proximal end attachable to a generally spherical head member, and a stem extending from said proximal end to a distal end and having a bend located there between, the stem having an enlarged portion for transferring axial loads from the stem directly to the resected surface of the femoral neck and
    a guide having an interior axial passageway adapted to house at least a portion of said stem adjacent said proximal end of said stem but below said bend, said portion of said stem being of uniform cross section along its length, and said interior axial passageway being without any taper, and said passageway having interior walls shaped to permit free axial movement between said portion of said stem and said guide but restricting any rotational or toggling movement between said stem and said guide.

18. The insert system of claim 17 wherein said enlarged portion is sized for contacting said resected surface of said femur at an outer cortical bone section.

19. The insert system of claim 18 wherein said enlarged portion has an undersurface having means conducive to bone ingrowth.

* * * * *